(12) United States Patent
Ratner et al.

(10) Patent No.: US 9,198,957 B2
(45) Date of Patent: Dec. 1, 2015

(54) **TREATMENT AND PREVENTION OF BACTERIAL VAGINOSIS AND *GARDNERELLA VAGINALIS* INFECTIONS**

(75) Inventors: Adam J. Ratner, New York, NY (US); Saul Hymes, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 13/982,675

(22) PCT Filed: Jan. 30, 2012

(86) PCT No.: PCT/US2012/023185
§ 371 (c)(1),
(2), (4) Date: Jul. 30, 2013

(87) PCT Pub. No.: WO2012/106264
PCT Pub. Date: Aug. 9, 2012

(65) Prior Publication Data
US 2013/0309219 A1 Nov. 21, 2013

Related U.S. Application Data

(60) Provisional application No. 61/438,231, filed on Jan. 31, 2011.

(51) Int. Cl.
*A61K 38/46* (2006.01)
*A61K 45/06* (2006.01)
*A61K 31/4164* (2006.01)
*A61K 31/4178* (2006.01)
*A61K 31/7056* (2006.01)
*A61K 9/00* (2006.01)

(52) U.S. Cl.
CPC .............. *A61K 38/465* (2013.01); *A61K 9/0034* (2013.01); *A61K 31/4164* (2013.01); *A61K 31/4178* (2013.01); *A61K 31/7056* (2013.01); *A61K 45/06* (2013.01)

(58) Field of Classification Search
None
See application file for complete search history.

(56) References Cited

U.S. PATENT DOCUMENTS

| 2003/0044403 | A1* | 3/2003 | Shak ........................ 424/94.61 |
| 2004/0023848 | A1 | 2/2004 | Boehm |
| 2008/0160065 | A1* | 7/2008 | Halliday et al. .............. 424/433 |
| 2009/0202516 | A1 | 8/2009 | Olmstead |
| 2011/0129454 | A1 | 6/2011 | Olmstead |

FOREIGN PATENT DOCUMENTS

WO WO2009/117373 A2 9/2009

OTHER PUBLICATIONS

SHanker, S., Toohey, M., and Munro, R. "In Vitro Activity of Seventeen Antimicrobial Agents against *Gardnerella vaginalis*", European Journal of Clinical Microbiology and Infectious Diseases 1982, vol. 1, pp. 298-300.*
ISA/US, "International Search Report and Written Opinion," Jun. 14, 2012, pp. 1-8.
Tetz, George V., "Effect of DNase and Antibiotics on Biofilm Characteristics", Antimicrobial Agents and Chemotherapy, Mar. 2009, pp. 1204-1209, vol. 53, No. 3, Publisher: American Society for Microbiology, Published in: http://www.ncbi.nlm.nih.gov/pmc/articles/PMC2650517/.

* cited by examiner

*Primary Examiner* — Renee Claytor
*Assistant Examiner* — Michelle F Paguio Frising
(74) *Attorney, Agent, or Firm* — Judith A. Evans; Beusse Wolter Sanks & Maire, PLLC

(57) ABSTRACT

*G. vaginalis* infection, a major cause of bacterial vaginosis (BV), is associated with biofilm formation. The present invention relates to treatment of *G. vaginalis* infections and BV with DNase. DNase reduces biofilm formation and increases biofilm breakdown, both in a dose dependent manner. The present invention further relates to treating BV and *G. vaginalis* infections with a combination of DNase and an antibiotic known to treat these diseases.

7 Claims, 18 Drawing Sheets

Dose-response inhibition of Strain 49145 biofilm formation by DNase

Dose-response Breakdown of Established Strain 49145 Biofilm by DNase

Heat-Inactivation of DNase Eliminates This Effect

Additive inhibition of Strain 49145 biofilm formation by a combination treatment with metronidazole and DNase Synergistic inhibition of Strain ARG3 biofilm formation by metronidazole and DNase

* = p<.001

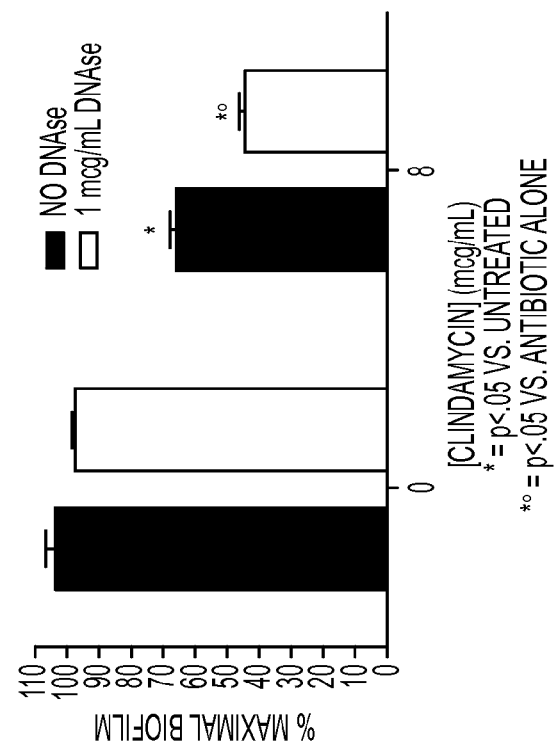
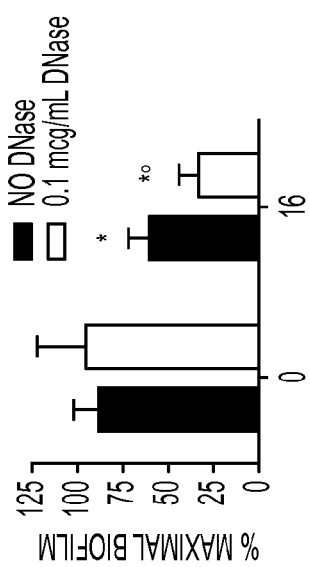
FIG. 8B
FIG. 8A

Synergistic breakdown of Strain 49145 biofilm by metronidazole and DNase

Synergistic breakdown of Strain ARG3 biofilm by metronidazole and DNase

Inhibition of Strain ARG3 biofilm formation by clindamycin and DNase

DNase Liberates Bacteria Into the Supernatant From Established ATCC *G. Vaginalis* Strain 49145 Biofilm DNase Liberates Bacteria Into the Supernatant From Forming ATCC *G. Vaginalis* Strain 49145 Biofilms

Supernatant Bacteria More Readily Killed By Metronidazole

ATCC *G. Vaginalis* Strain 49145 Biofilms

Supernatant

DNase-sensitive Group B *Streptococcus* biofilms demonstrated by spectrophotometry

TREATMENT AND PREVENTION OF BACTERIAL VAGINOSIS AND *GARDNERELLA VAGINALIS* INFECTIONS

STATEMENT OF GOVERNMENTAL INTEREST

This invention was made with Government support under Grant AI092743 awarded by the National Institutes of Health. The Government has certain rights in the invention.

CROSS-REFERENCE TO RELATED APPLICATIONS

This application is a 371 application of International Patent Application Serial No. PCTUS12/23185 entitled "Treatment and Prevention of Bacterial Vaginosis and *Gardnerella Vaginalis* Infections," filed on Jan. 30, 2012, and claims the benefit of U.S. Provisional Patent Application Ser. No. 61/438,231 entitled "Treatment and Prevention of Bacterial Vaginosis and *Gardnerella Vaginalis* Infections," filed on Jan. 31, 2011, the specifications both of which are incorporated herein by reference.

BACKGROUND OF THE INVENTION

1. Field of the Invention

The present invention relates to the discovery that bacterial vaginosis (BV) can be treated by administering DNase alone or together with antibiotics that are known to treat BV.

2. Description of the Related Art

BV is the most common vaginal infection worldwide and is associated with significant adverse consequences including and preterm labor and delivery (40, 41), post-partum endometritis, (42) and an increased risk of HIV acquisition. (43-45). Reported prevalence rates range from 10-40% depending upon the population studied. (46). However, suboptimal methods of diagnosis and a high percentage of asymptomatic patients make the true prevalence of BV difficult to ascertain. *Gardnerella vaginalis* (*G. vaginalis*), is a bacterial species associated with BV.

The pathogenesis of BV remains poorly understood. It is most commonly defined as a pathological state characterized by the loss of normal vaginal flora, particularly species of $H_2O_2$-producing species of *Lactobacillus*, and overgrowth of other microbes including *G. vaginalis, Mobiluncus* species, and *Mycoplasma hominis*. Recent data however, suggest a primary role for *G. vaginalis* as a specific and sexually transmitted etiological agent in BV, as was initially postulated by Gardner and Dukes in 1955. (47-49).

Alterations of both local host immunity and the genital tract microflora appear to contribute to the pathogenesis of BV (39), which can be difficult to eradicate even using targeted antimicrobial therapy (4). In addition, randomized trials of antibiotics for the prevention of BV-associated preterm birth have not shown consistently beneficial effects, suggesting that host inflammatory responses set in motion early in the course of the disease may contribute significantly to the consequences of infection (26, 27).

In the 1950s, Leopold (25) and then Gardner and Dukes (14) observed abundant small, pleomorphic gram-variable rods in the genital tract of women with BV. This organism, first called *Haemophilus vaginalis* (13) and repeatedly renamed as more information about its characteristics became available (reviewed in (5)), is now classified as *G. vaginalis*, the sole member of the genus *Gardnerella* (16, 30). Phylogenetic analysis based on 16S rRNA places *Gardnerella* in the gram-positive family Bifidobacteriales. An abundance of *G. vaginalis* and a paucity of *Lactobacillus* species are characteristic of a BV-associated microflora. *G. vaginalis* is present in essentially all cases of BV but can also be detected in a minority of asymptomatic women (1). Likewise, several groups have demonstrated that the vaginal microflora is exceedingly complex in BV where the vaginal mucosa is host to many non-*Gardnerella* organisms (12, 18, 20); however, recent studies have provided additional evidence for *G. vaginalis* as the primary etiologic agent of BV. (61-63; 78).

BV is exceedingly common, especially in Africa where more than 50% of women in numerous trials, (including the recent trial of acyclovir for HSV suppression in Tanzania) were infected with BV. BV has been repeatedly associated with both increased risk of HIV acquisition and increased viral shedding among those already infected with HIV. In vitro treatment of HIV-infected cells with *Gardnerella* leads to increased production of HIV viral transcripts.

BV, a chronic infectious/inflammatory disease associated with preterm birth, is strongly linked with the mucosal overgrowth of *G. vaginalis* and its attachment to epithelial cells. (78). BV has also been referred to in the literature as bacterial vaginosis, non-specific vaginitis, non-specific vaginosis, and bacterial vaginitis; and *G. vaginalis* has been called *Haemophilus vaginalis* and *Corynebacterium vaginale*. BV is caused by a profound shift in the bacteria colonizing the vagina, with overgrowth of a variety of species, most prominently *G. vaginalis*. During BV, the epithelial surface is covered with a dense collection of *G. vaginalis* in a biofilm that is frequently recalcitrant to treatment. Even in women for BV with oral or intravaginal antibiotics, the rate of recurrence approaches 50% at 6 months.

Therefore, there is a great need for a new methods and compositions to treat and prevent *G. vaginalis* infections and BV, with benefits of reducing preterm delivery and minimizing the risk of transmitting HIV from person to person, particularly from an HIV-positive mother who has BV or a *G. vaginalis* infection to a fetus or an infant during delivery.

SUMMARY OF THE INVENTION

It has been discovered that treatment of *G. vaginalis* biofilms with DNase reduces biofilm formation and increases biofilm breakdown, both in a dose dependent manner. The combination of DNase and an antibiotic that is effective in treating BV have an additive and synergistic effect to reduce biofilm formation. In addition, the combination has a synergistic effect in increasing biofilm breakdown in three different strains of *G. vaginalis*. Therefore, DNase can be administered alone or together with antibiotics to treat *G. vaginalis* and BV. Antibiotics commonly used to treat BV and *G. vaginalis* infections include metronidazole, clindamycin and tinidazole.

In a first set of embodiments, the invention is directed to a method of treatment of BV or *G. vaginalis* infections by administering to an infected subject a therapeutically effective amount of DNase alone or in combination with one or more antibiotics that are effective in treating BV. When administered in combination, the two drugs can be administered in a single formulation or in separate formulations, either simultaneously or at different times, by the same route or by different routes. Because of the potential for nonspecific DNA lysis of unintended targets, DNase is only administered locally, for example as a vaginal suppository, not systemically. The antibiotic can be administered locally or systemically or both. In an embodiment, a single dose of DNase is from about 1 μg to about 25 mg and is administered locally to the vagina typically at least once a day. DNase can be formulated like Pulmozyme® in a sterile, clear, colorless, aqueous solution containing the required dose. In an embodiment, DNase is formulated at 1.0 mg/ml in aqueous solution with 0.15 mg/ml calcium chloride dehydrate and 8.77 mg/ml sodium chloride with no preservative at a nominal pH of about 6.3. The DNase dose administered can be determined by adjusting the volume of the formulation that is administered.

In a second set of embodiments, a prophylactically effective amount of DNase is administered locally to the vagina to prevent BV or *G. vaginalis*, in high risk subjects, such as those having recurring infections, either alone or together with an antibiotic.

A third set of embodiments is directed to methods for treating or preventing other vaginal bacterial infections that are associated with biofilm formation as are encountered, for example, with *Atopobium* and *Mobiluncus* by administering DNase either alone or administered together with an antibiotic that is effective in treating the bacterial infection. Vaginal infections caused by *Staphylococcus aureus* and group B *Streptococcus* (GBS) can also be treated with DNase either alone or administered together with an antibiotic known to be effective against the particular bacteria. GBS is a part of normal flora of the gut and genital tract and is found in 20-40% women. Infection of this organism may result in neonatal death due to severe neonatal infection. It may also result in maternal death although this is only occasionally by causing upper genital tract infection which progresses to septicemia. GBS are sensitive to penicillin and ampicillin also cefazolin, clindamycin, erythromycin, or vancomycin. The United States uses the most effective strategy: all pregnant women are screened for GBS and prophylactic antibiotics are given to all women testing positive and to those who deliver before 37 weeks of pregnancy plus to women with unknown GBS test results and other recognized risk factors. (79). The treatment of choice for *S. aureus* infection is penicillin; other antibiotics include, penicillinase-resistant β-lactam antibiotic (e.g., oxacillin or flucloxacillin) or gentamicin.

A fourth set of embodiments is directed to pharmaceutical compositions and kits comprising DNase and one or more antibiotics that are effective in treating BV and *G. vaginalis* infections formulated for local administration to the vagina, preferably topical for administration as, for example, a vaginal suppository, cream, capsule, and gel. In certain embodiments the compositions are formulated for slow release to minimize the need for repeated delivery and to maintain a steady concentration of drugs.

A fifth set of embodiments of the invention are directed to methods for reducing transmission of HIV from an HIV/BV or *G. vaginalis*-infected woman to her sexual partner, or to an infant during childbirth by administering a therapeutically effective amount of DNase alone or in combination with one or more antibiotics.

In a sixth set of embodiments, the DNase and/or antibiotics are administered locally to the vagina. For example, administration can be (1) in pregnant women with BV or *G. vaginalis* infections to reduce the risk of preterm birth, (2) to prevent a sexually transmitted disease (STD), (3) to prevent postpartum endometritis in subjects with BV or *G. vaginalis* infections, or (4) to prevent postsurgical infection in subjects with BV or *G. vaginalis* infections, including but not limited to gynecological surgery.

These and other features, aspects, and advantages of the present invention will become better understood with regard to the following description, appended claims, and accompanying drawings.

BRIEF DESCRIPTION OF THE DRAWINGS

The present invention is illustrated by way of example, and not by way of limitation, in the Figures.

DESCRIPTION

Figure 1:
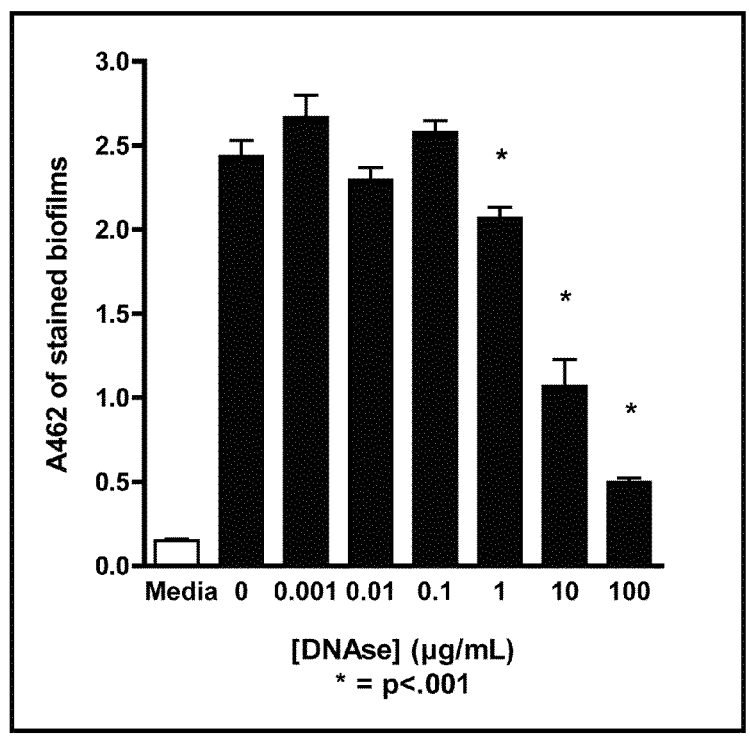
FIG. 1. Dose-response inhibition of *Gardnerella* strain 49145 biofilm formation by DNase administered at time=0 hours measured as absorbance at 462 nm.

In the following description, for the purposes of explanation, numerous specific details are set forth in order to provide a thorough understanding of the present invention. It will be apparent, however, to one skilled in the art that the present invention may be practiced without these specific details.

I. DEFINITIONS

Unless defined otherwise, all technical and scientific terms used herein have the same meaning as commonly understood by one of ordinary skill in the art.

The terms "individual," "subject" and "patient" are used interchangeably herein and refer to any mammalian subject for whom diagnosis, treatment, or therapy is desired, particularly humans. In the preferred embodiment, the subject is a human being.

A "therapeutically effective amount" of a compound is an amount that provides a therapeutic benefit in the treatment or management of a disease or condition such as BV or *G. vaginalis* infection, delays or minimizes one or more symptoms associated with the disease or condition, or enhances the therapeutic efficacy of another therapeutic agent. An agent is the to be administered in a "therapeutically effective amount" if the amount administered results in a desired change in the physiology of a recipient mammal, (e.g. decreases one or more symptoms of the BV or *G. vaginalis*, or decreases the amount of *G. vaginalis* in a biological sample taken from the patient to a level that is at least about 10% less than the level before drug treatment.

"Delaying" the onset of a disorder shall mean slowing the progression of the disorder, or extending the time before the onset begins.

"Prophylactically effective amount" means an amount sufficient to inhibit the onset of a disorder or a complication associated with a disorder in a subject.

As used herein, the term "biofilm" refers to bacteria that attach to surfaces aggregate in a hydrated polymeric matrix of their own synthesis. A biofilm is an aggregate of microorganisms in which cells adhere to each other on a surface. These adherent cells are frequently embedded within a self-produced matrix of extracellular polymeric substance (EPS). Biofilm EPS, which is also referred to as slime (although not everything described as slime is a biofilm), is a polymeric conglomeration generally composed of extracellular DNA, proteins, and polysaccharides.

A deoxyribonuclease ("DNase") is any enzyme that catalyzes the hydrolytic cleavage of phosphodiester linkages in the DNA backbone. A wide variety of deoxyribonucleases are known, which differ in their substrate specificities, chemical mechanisms, and biological functions. Deoxyribonuclease I (usually called DNase I), is an endonuclease coded by the human gene DNASE1. DNase I is a nuclease that cleaves DNA preferentially at phosphodiester linkages adjacent to a pyrimidine nucleotide, yielding 5'-phosphate-terminated polynucleotides with a free hydroxyl group on position 3', on average producing tetranucleotides. It acts on single-stranded DNA, double-stranded DNA, and chromatin.

"Administering" shall mean delivering in a manner which is effected or performed using any of the various methods and delivery systems known to those skilled in the art. Administering can be performed, for example, topically (for DNase delivery to the vagina), or for the antibiotics: intravenously, orally, via implant, transmucosally, transdermally, intradermally, intramuscularly, subcutaneously, or intraperitoneally. Administering can also be performed, for example, once, a plurality of times, and/or over one or more extended periods.

"Concurrent" administration of two agents shall mean administration wherein the time period over which the first agent is administered either overlaps with, or is coincident with, the time period over which the second agent is administered. For example, a first and a second agent are concurrently administered if the first agent is administered once per week for four weeks, and the second agent is administered twice per week for the first three of those four weeks. Likewise, for example, a first and second agent are concurrently administered if the first and second agent are each administered, in the same or separate formulations, on the same day, once per week for four weeks.

"Agent" means DNase and any antibiotic that treats or prevents BV, *G. vaginalis, Atopobium, Mobiluncus*, and other vaginal bacteria that may overgrow to deleterious levels, and other pathogens such as *Staphylococcus aureus* and group B *streptococcus* infections.

"Treating" a subject afflicted with a disorder shall mean causing the subject to experience a reduction, delayed progression, regression or remission of the disorder and/or its symptoms. In one embodiment, recurrence of the disorder and/or its symptoms is prevented. In the preferred embodiment, the subject is cured of the disorder and/or its symptoms.

Overview

Many bacterial species may grow as complex, multicellular communities known as biofilms. (73). BV, *G. vaginalis, Atopobium, Mobiluncus, Staphylococcus aureus* and group B *Streptococcus* are associated with biofilm formation and long-term colonization of the vaginal mucosal surface. Biofilms are generally composed of bacteria encased within an extracellular matrix that provides structure and environmental resistance to the community. It has become increasingly clear that bacterial biofilms represent a major challenge in clinical medicine. Such infections may be exceedingly difficult to eradicate, as the biofilm matrix provides a significant barrier to both immune effectors and antibiotic agents.

It is thought that the relative insensitivity of biofilm organisms to antibiotic therapy may be a contributing factor to recurrence of BV and other bacterial infections that are associated with biofilm formation. Numerous studies in multiple species, including *N. meningitidis, S. aureus*, and *E. faecalis*, have demonstrated a role for extracellular DNA (eDNA) in biofilm structure. DNA represents an important component of the biofilm matrix. It was shown by Swidsinski et al. that *G. vaginalis* forms a biofilm in vivo that persists after standard therapies and even after resolution of symptoms.

*G. vaginalis* Pathophysiology

Certain lactobacilli produce $H_2O_2$ and lactic acid, which normally suppress growth of anaerobes. However, in bacterial vaginosis, *G. vaginalis* and other anaerobes proliferate and the number of lactobacilli decreases. Patterson, et al. developed an in vitro model for *G. vaginalis* biofilm formation and compared susceptibilities of biofilms vs. planktonic cultures to $H_2O_2$ and lactic acid. A study of the structure and composition of the biofilm matrix revealed that biofilms tolerated 4-8 fold higher concentrations of $H_2O_2$ and lactic acid (respectively) than did planktonic cultures, and determined that the increased tolerance contributed to the resistance of the biofilm to antibiotic treatment and the survival of *G. vaginalis* in the presence of lactobacilli. They also showed that treatment of biofilms with the protease significantly reduced the sensitivities for $H_2O_2$ and lactic acid. Patterson, et al., Effect of biofilm phenotype on resistance of *G. vaginalis* to hydrogen peroxide and lactic acid, Am. J. Obstet. Gynecol 2007; 197:170.e1-170.e7. Patterson also tested the effect of DNase treatment on biofilms made by *G. vaginalis*, but saw no reduction in biofilm formation or breakdown.

II. DESCRIPTION OF EMBODIMENTS OF THE INVENTION

The effect of DNase, specifically bovine pancreatic DNase, on biofilm formation and degradation was studied. It is important to note that any DNase may be used in the present inventions, including bovine, human DNase, and *Gardnerella* DNase. Biofilms made by two different strains of *G. vaginalis* were either (1) stained with safranin, solubilized and analyzed for safranin absorbance at A462 nm measured with a spectrophotometer, or (2) biofilms were also grown in chamber slides and DAPI staining was performed for fluorescence microscopy.

Figure 2:
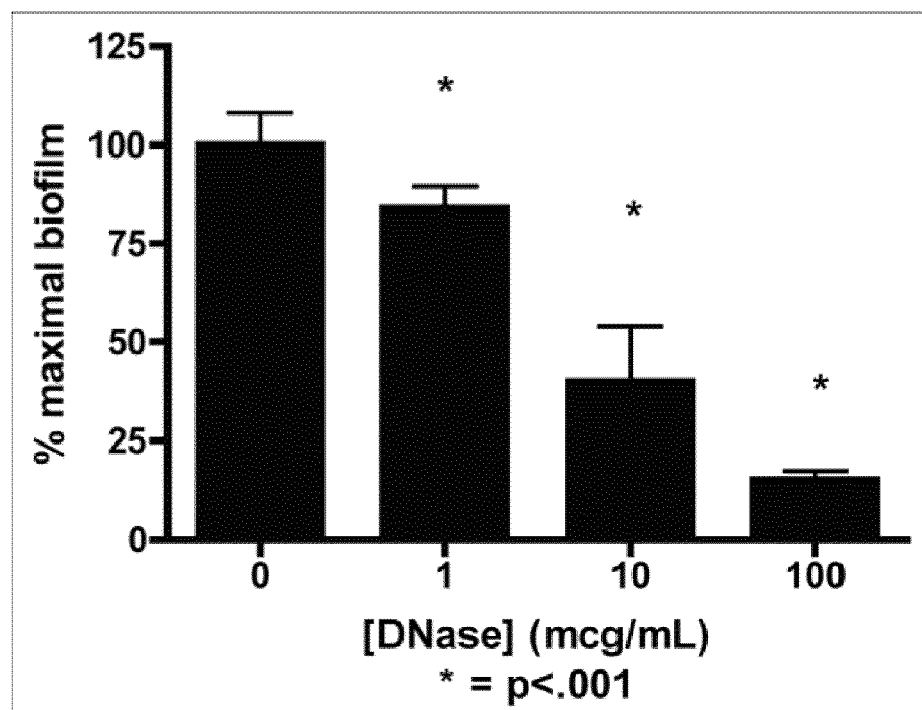
FIG. 2. DNase inhibits strain ARG3 biofilm formation at 1 μg/ml; 10 μg/ml and 100 μg/ml concentrations.
Figure 3:
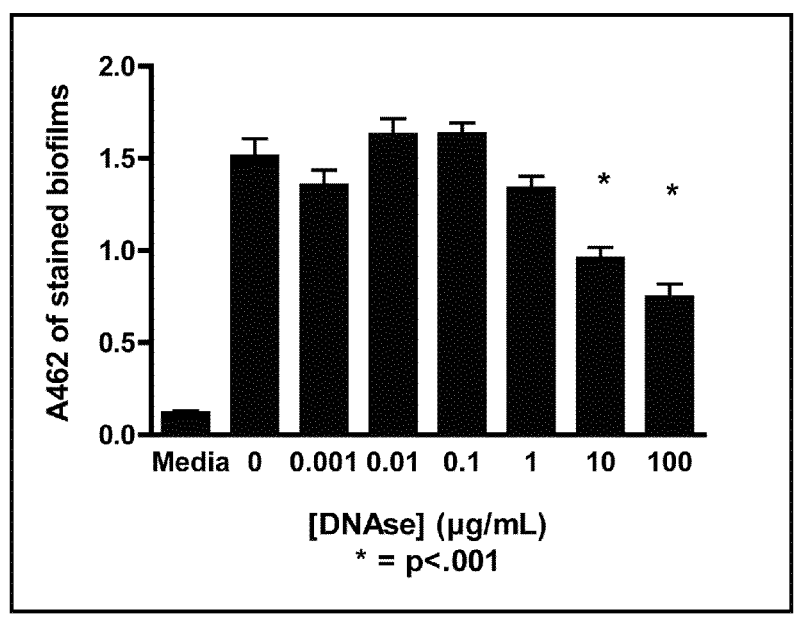
FIG. 3. Dose-response breakdown of established *Gardnerella* strain 49145 biofilms by DNase at 0.001 μg/ml; 0.01 μg/ml; 0.1 μg/ml; 1 μg/ml; 10 μg/ml; and 100 μg/ml concentrations administered at t=24 hours measured as absorbance at 462 nm.
Figure 4:
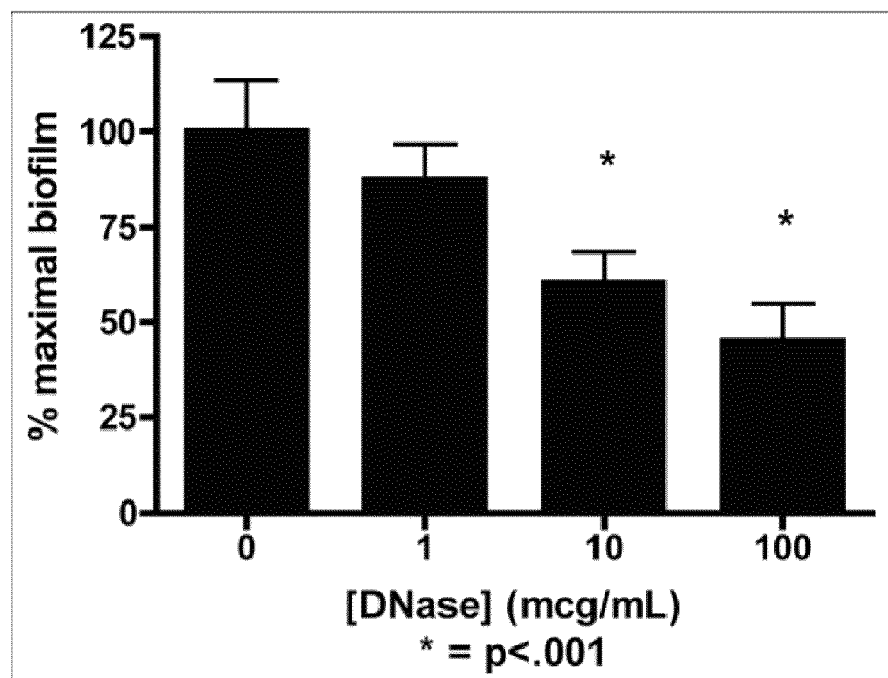
FIG. 4. DNase breaks down 24-hour formed strain ARG3 biofilms at 1 μg/ml; 10 μg/ml; and 100 μg/ml concentrations.
Figure 5:
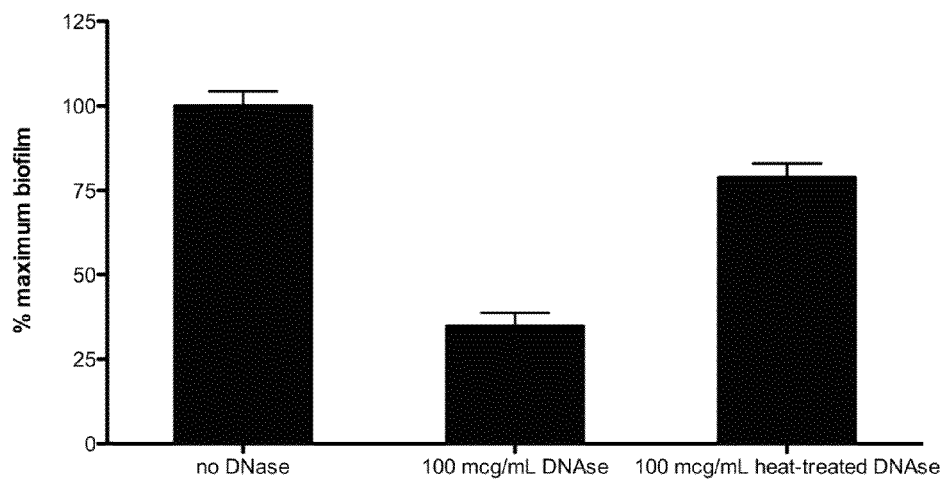
FIG. 5 is a graph illustrating the elimination effect of heat-inactivation of DNase.
Figure 17:
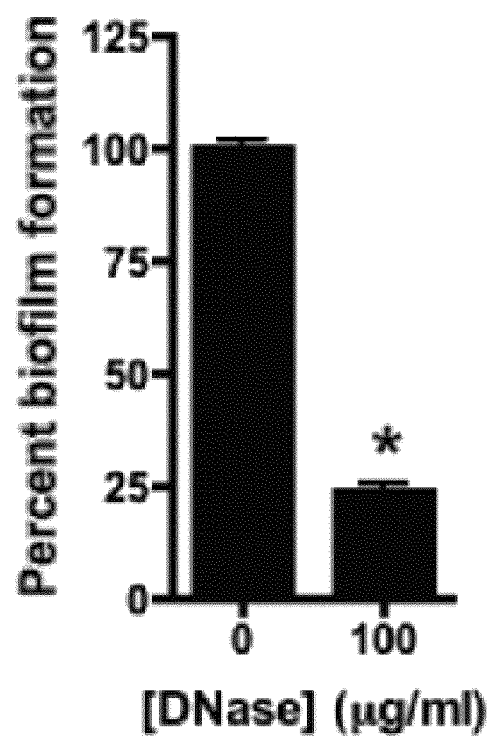
FIG. 17 is a graph illustrating DNase-sensitive group B *Streptococcus* biofilms demonstrated by spectrophotometry.

The experiments summarized herein are discussed in more detail in the Examples. Example 1 shows that DNase treatment reduced *G. vaginalis* biofilm formation in two strains of *G. vaginalis*: strain 49145 and strain ARG3. FIGS. 1 and 2. There is also a dose-response inhibition of group B *Streptococcus* biofilm formation by DNase. FIG. 17. It was also discovered that DNase increased biofilm breakdown in a dose-dependent manner. FIGS. 3 and 4. Heat inactivation of DNase eliminates this effect. FIG. 5.

Importantly, there was also at least an additive—and more often—a synergistic effect on biofilm formation when DNase and either metronidazole and clindamycin are administered together. FIGS. 6-12.

Figure 6:
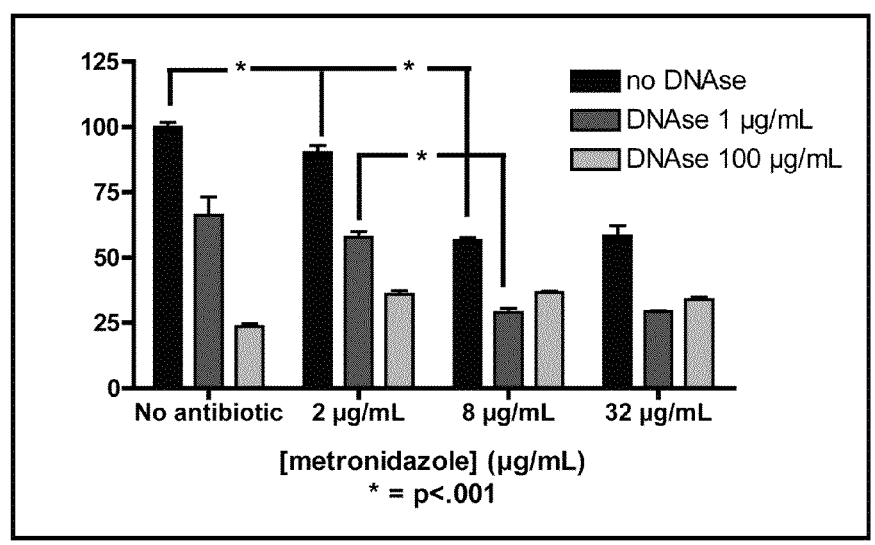
FIG. 6 is a graph showing the additive inhibition of strain 49145 biofilm formation by a combination treatment with metronidazole at 2 μg/ml; 8 μg/ml; and 16 μg/ml concentrations and DNase at t=0 hrs at 1 μg/ml; and 100 μg/ml concentrations.
Figure 7:
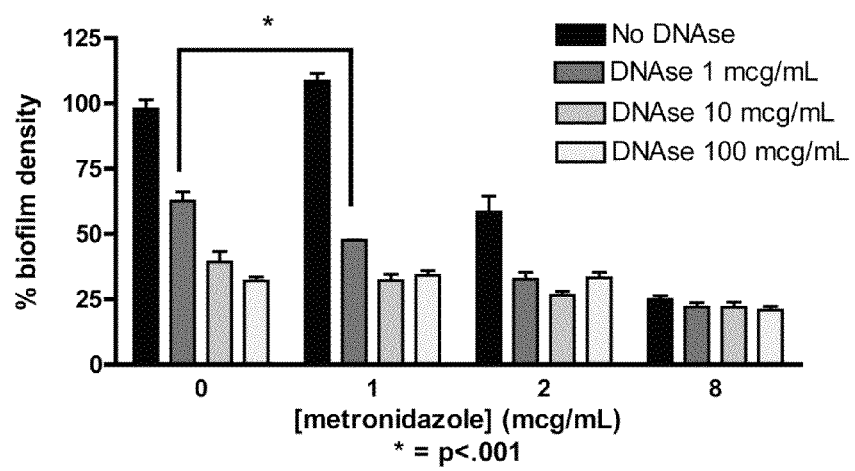
FIG. 7 is a graph showing the synergistic inhibition of strain ARG3 biofilm formation by a combination treatment with metronidazole at 1 μg/ml; 2 μg/ml; and 8 μg/ml concentrations and DNase at t=0 hrs at 1 μg/ml; 10 μg/ml; and 100 μg/ml concentrations.

An additive inhibition of strain 49145 biofilm formation was seen by a combination treatment with metronidazole and DNase. FIG. 6. Synergistic inhibition of strain ARG3 biofilm formation was also observed. FIG. 7.

Figure 8D:
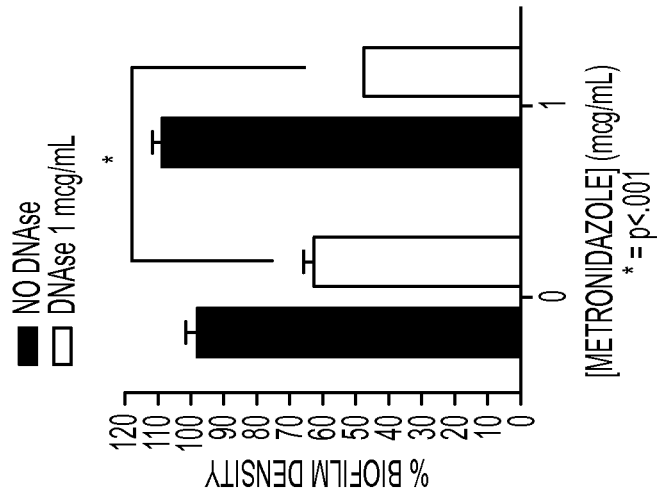
FIG. 8 (A)-(D): is a series of graphs showing the synergistic inhibition of biofilm formation by a combination treatment with clindamycin and DNase at t=0 hours in strain 49145 (A) and strain ARG3 (B) and treatment with metronidazole and DNase at t=0 hours in strain 49145 (C) and strain ARG3 (D).
Figure 8C:
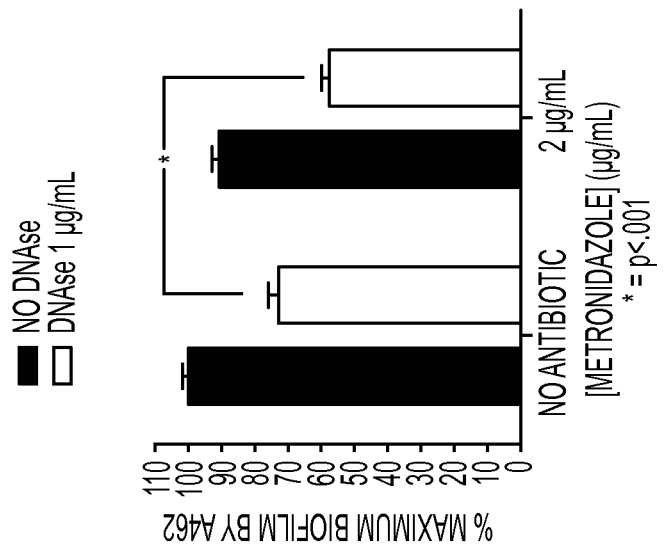
Figure 9:
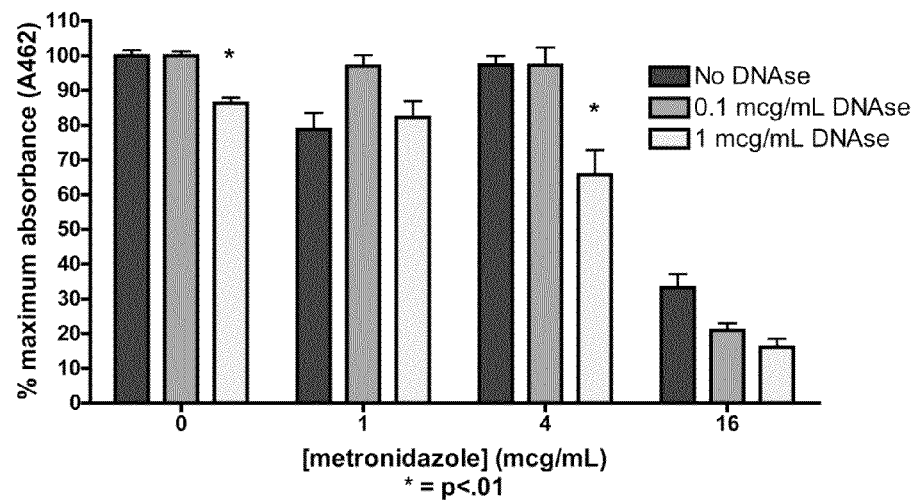
FIG. 9 is a graph showing the synergistic breakdown of strain 49145 biofilm by a combination treatment with metronidazole at 1 μg/ml; 4 μg/ml; and 16 μg/ml concentrations and DNase at t=24 hrs at 0.1 μg/ml; and 1 μg/ml concentrations.
Figure 10:
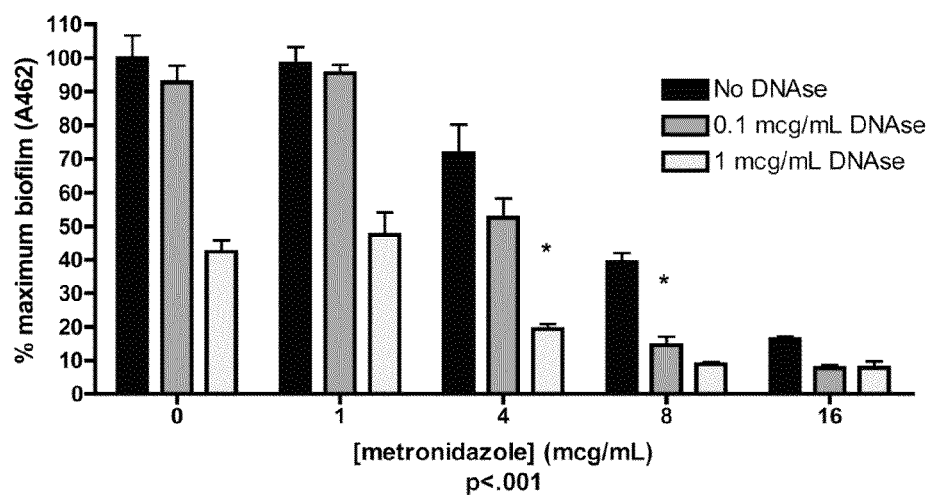
FIG. 10 is a graph illustrating the synergistic breakdown of strain ARG3 biofilm by a combination treatment with metronidazole at 1 μg/ml; 4 μg/ml; 8 μg/ml; and 16 μg/ml concentrations and DNase at t=24 hrs at 0.1 μg/ml; and 1 μg/ml concentrations.
Figure 11:
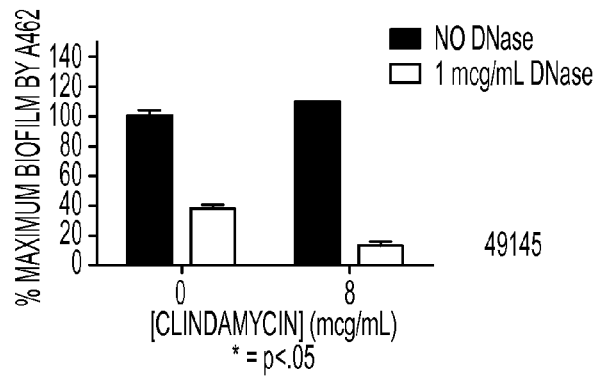
FIG. 11 (A)-(C) is a series of graphs illustrating the synergistic breakdown of established strain 49145 biofilm (A)-(B) by a combination treatment with (A) clindamycin and DNase and (B) metronidazole and DNase and (C) the synergistic breakdown of established strain ARG3 biofilm by a combination treatment with metronidazole and DNase.
Figure 11:
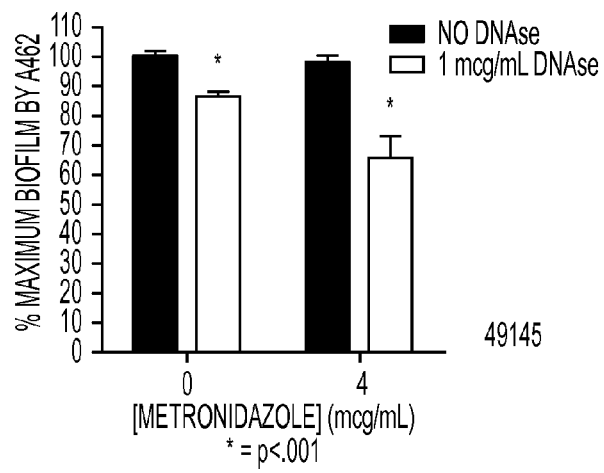
Figure 11:
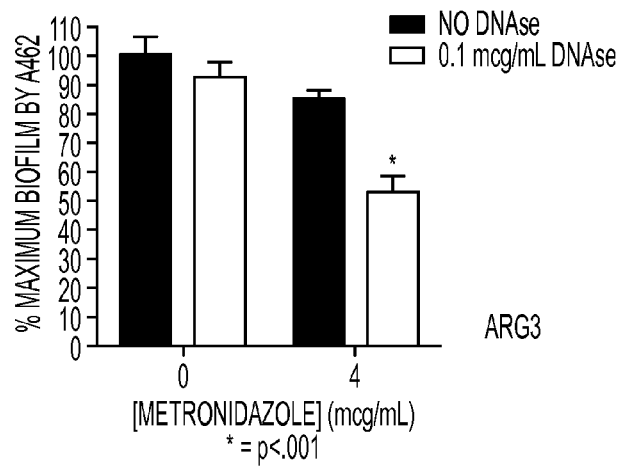
Figure 12:
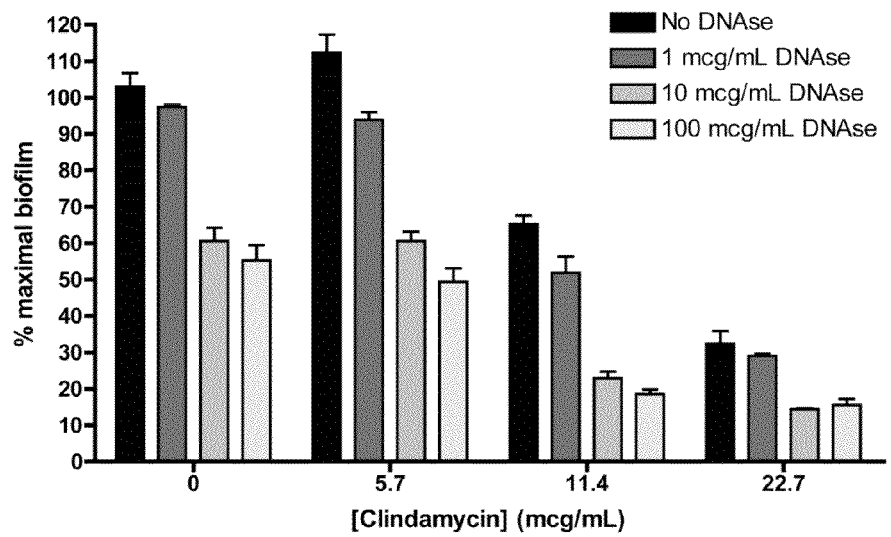
FIG. 12 is a graph illustrating the synergistic/additive inhibition of strain ARG3 biofilm formation by a combination treatment with clindamycin at 5.7 μg/ml; 11.4 μg/ml; and 22.7 μg/ml and DNase at 1 μg/ml; 10 μg/ml; and 100 μg/ml concentrations.

Synergistic inhibition of biofilm formation in both strains was seen with DNase and clindamycin. FIGS. 8 and 12. There was also a synergistic increase in the breakdown of strain 49145 and strain ARG3 biofilms by metronidazole and DNase FIGS. 9 and 10, respectively, and clindamycin FIG. 11.

Figure 13:
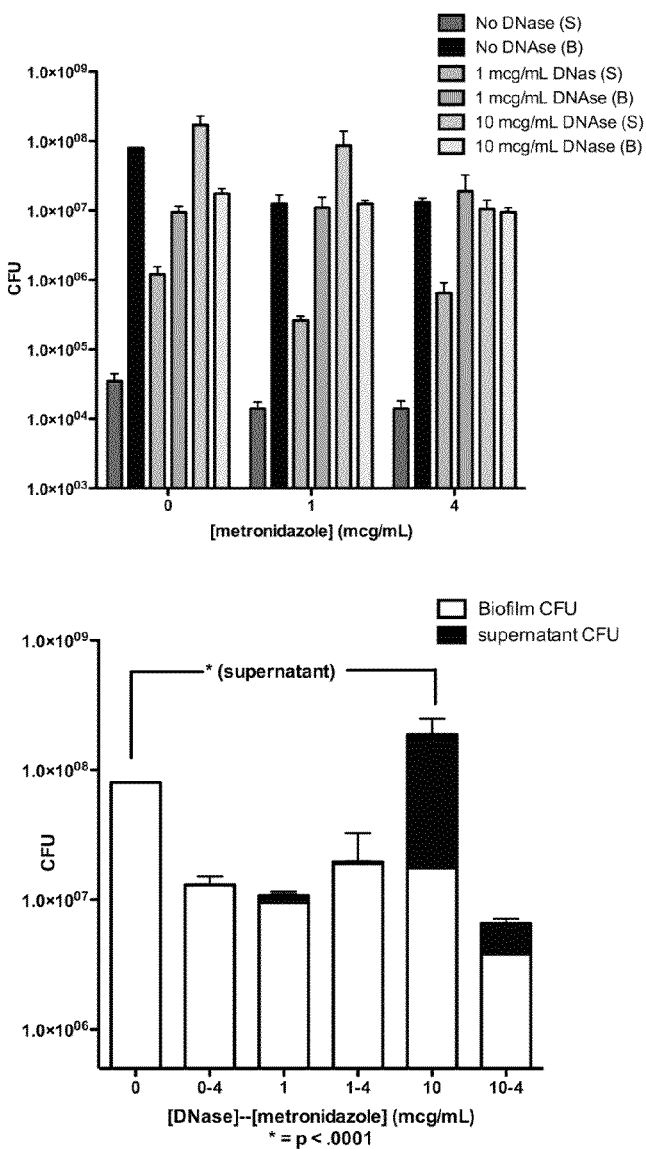
FIG. 13 (A)-(B) is a series of graphs illustrating the liberation of bacteria into the supernatant from an established ATCC *Gardnerella* strain 49145 biofilm with the treatment of DNase and metronidazole.
Figure 14:
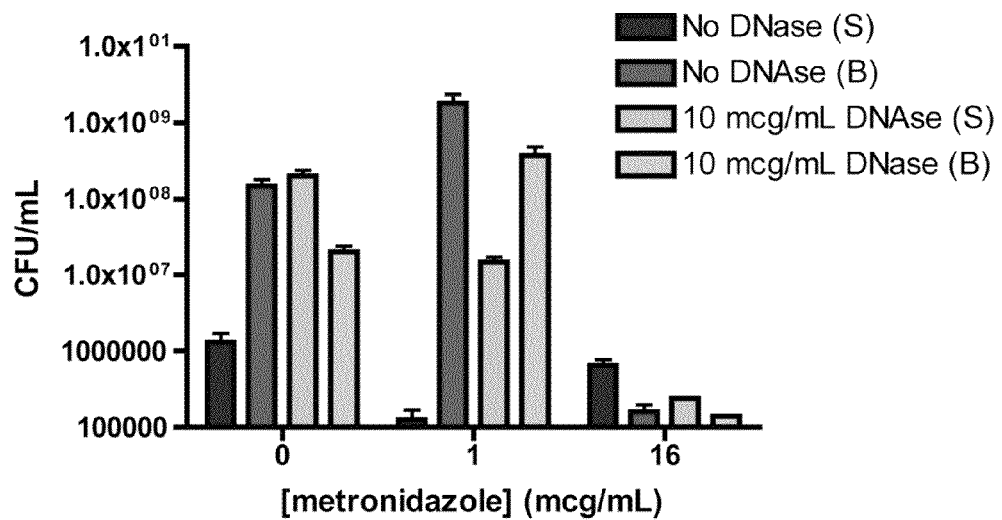
FIG. 14 is a graph illustrating the liberation of bacteria into the supernatant from forming ATCC *Gardnerella* strain 49145 biofilms with the treatment of DNase and metronidazole.
Figure 15:
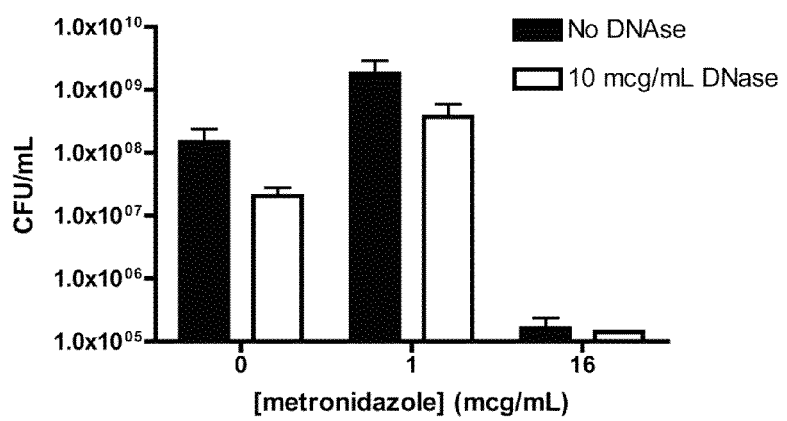
FIG. 15 is a graph illustrating supernatant bacterial more readily killed by metronidazole. Biofilms are ATCC *Gardnerella* strain 49145.
Figure 15:
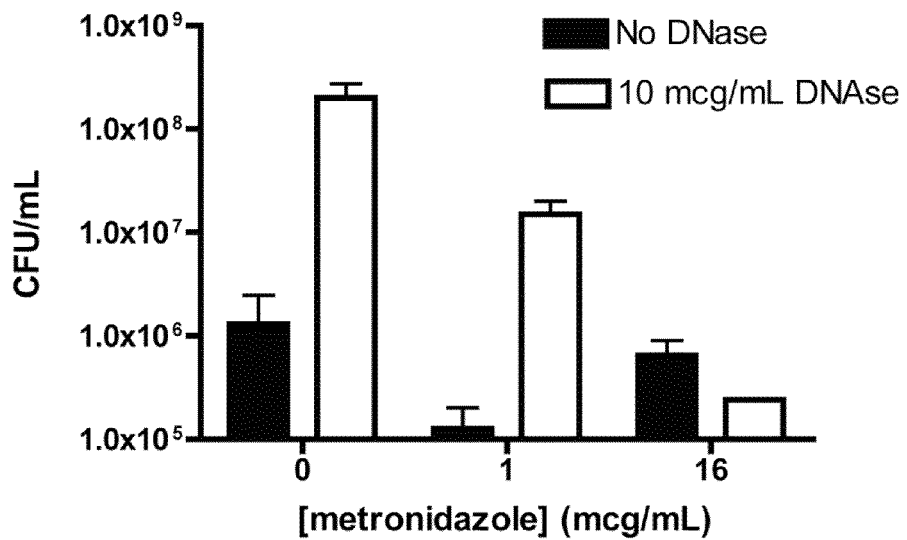

One reason for the synergism may be due to the observation described in Example 3 showing that DNase liberates bacteria into the supernatant from established biofilms. FIGS. 13 and 14. This result shows that treatment with DNase did not reduce the number of bacteria in the biofilm cultures overall. In other words, DNase did not kill the bacteria. Without being bound by theory, the release of the bacteria by DNase may account for the synergism seen when DNase and antibiotics are administered together because the released bacteria are more accessible to the antibiotic which in turn kills them. FIG. 15. Because DNase should prevent significant biofilm formation and/or should promote the release of bacteria from any biofilm that forms, the bacteria more vulnerable to the body's own immune system, even without antibiotic therapy.

Biofilm breakdown or dissolution has the advantage of increasing the rate of expulsion of bacteria from the vagina by the natural flow of mucous, and it may also increase the susceptibility of the bacteria to the natural immune defenses and antibiotics.

Figure 16:
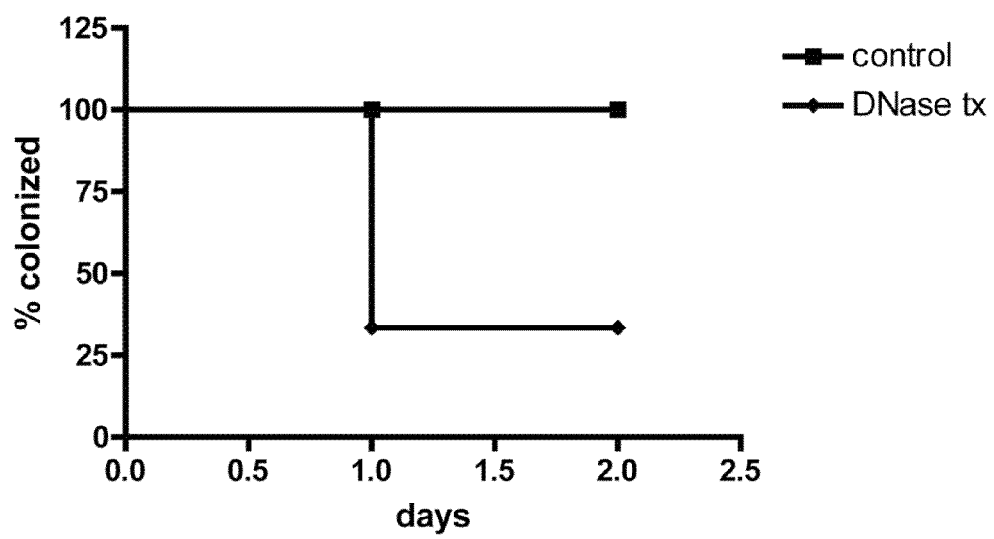
FIG. 16 is a graph illustrating the decrease in mouse colonization rate in strain ARG37 with the treatment of DNase.

It was further discovered that DNase decreased the rate of colonization by strain ARG37 in mice. FIG. 16.

Based on these discoveries, certain embodiments of the invention are directed to treatment of BV or *G. vaginalis* infections by administering a therapeutically effective amount of DNase alone or in combination with therapeutically effective amounts of one or more antibiotics known to treat BV and *G. vaginalis* infections.

Antibiotic Treatment

*G. vaginalis* is most properly grouped with the gram-positives, despite its variable staining characteristics (36). Antibiotics that have been used to treat BV and *G. vaginalis* infections include metronidazole, clindamycin and tinidazole. Metronidazole is the most successful therapy for BV and *G. vaginalis* infections. Most comparative studies using multiple divided-dose oral regimens for one week achieved early rates of clinical cure in excess of 90 percent, and cure rates (by Amsel criteria) of approximately 80 percent at four weeks. A randomized trial showed that short-term cure rates were significantly higher when the initial course of metronidazole therapy was 14 days rather than 7 days. (75). However, long-term cure rates (21 days after completion of therapy) were similar for both treatment regimens. In one embodiment, the oral regimen of tinidazole is 500 mg twice daily for seven days. (76). Topical vaginal therapy with 0.75 percent metronidazole gel (5 g once daily for five days) is as effective as oral metronidazole. The choice of oral versus topical therapy depends upon patient or provider preference.

Clindamycin can be used as a topical vaginal therapy with 2 percent clindamycin cream (5 g of cream containing 100 mg of clindamycin phosphate) as a seven-day regimen. Alternative regimens include oral clindamycin (300 mg twice daily for seven days) or clindamycin ovules (100 mg intravaginally once daily for three days) (76). Vaginal clindamycin and oral metronidazole for bacterial vaginosis: a randomized trial. Obstet Gynecol 2000; 96:256). A one-day or single application of clindamycin as a bioadhesive has also been approved by the FDA (Clindesse). These regimens have not been studied extensively and may have lower efficacy for eradicating BV.

Tinidazole is a second generation nitroimidazole. It has a longer half-life than metronidazole (12 to 14 hours versus 6 to 7 hours) and fewer side effects (77). In one embodiment, 1 gram of tinidazole is administered orally once daily for five days, as efficacy is slightly higher and side effects are slightly less frequent than with shorter course therapy (tinidazole 2 grams orally daily for two days).

Methods of Treatment

Certain embodiments of the invention are directed to treatment of BV or *G. vaginalis* infections by administering to an infected subject a therapeutically effective amount of DNase alone or in combination with one or more antibiotics known to treat BV, *G. vaginalis* or other infection being targeted. When administered in combination, the two drugs can be administered topically to the vagina in a single formulation or in separate formulations (where the antibiotic is administered systemically), either simultaneously or at different times, by the same route or by different routes. Because of the potential for nonspecific DNA lysis of unintended targets, DNase is only administered locally, for example as a vaginal suppository, not systemically. The antibiotic can be administered locally or systemically.

Routine experimentation will determine the optimum amount, and frequency of administration of DNase. Antibiotic treatment of BV and *G. vaginalis* is well known and the amounts described above are suggested doses. However, it is possible that the amount of antibiotic may be reduced when it is administered together with DNase.

In some embodiments a therapeutically effective amount of DNase is administered locally to the vagina, typically once or twice daily. DNase has been used therapeutically to treat other diseases such as cystic fibrosis. Pulmozyme®, a synthetic version of the naturally occurring human deoxyribonuclease I, is often prescribed to help improve lung function in people with cystic fibrosis at a recommended dose of 2.5 mg by inhalation. Recommended therapeutic doses of DNase for use in embodiments of the present invention for local administration to the vagina are from about 1 µg to about 25 mg.

In certain embodiments the dose is from about 1 mg to about 5 mg to treat BV and *G. vaginalis* infections, as well as the other vaginal infections caused by bacteria that form biofilms (*Atopobium, Mobiluncus, Staphylococcus aureus*, group B *Streptococcus*). *Atopobium vaginae* responds using the Etest to low concentrations of clindamycin (range: <0.016 µg/ml), rifampicin (<0.002 µg/ml), azithromycin (<0.016-0.32 µg/ml), penicillin (0.008-0.25 µg/ml), ampicillin (<0.016-0.94 µg/ml), ciprofloxacin (0.023-0.25 µg/ml) and linezolid (0.016-0.125 µg/ml). A variable susceptibility for metronidazole was found, ranging from 2 to more than 256 µg/ml. (80).

The presence of *Mobiluncus* spp. (*M. curtisii* and *M. Mulieris*) in the vagina is highly specific although not sensitive for the diagnosis of BV. Of the two, *M. Curtisii* appears to predominate. Results of in vivo treatment of humans showed that clindamycin reduces vaginal *Mobiluncus morphotypes* to a greater extent than metronidazole in patients with BV (clindamycin vaginal single-dose cream (CVSDC) or metronidazole vaginal gel (MVG) were tested.) (81).

Many factors affect the therapeutically effective dose of the DNase including the severity of the infection, other medicines the subject is taking, the type of pharmaceutical formulation, and other medical conditions. If administered for prophylactic use, the amount of DNase may be considerably lower, for example in the microgram range.

Certain other embodiments are directed to methods of preventing BV and *G. vaginalis* by administering a prophylactically effective amount of DNase topically to the vagina, alone or together with antibiotics to subjects at high risk, including but not limited to those who suffer from recurrent BV, pregnant women, those who suffer from recurrent sexually transmitted diseases [STDs], and those who are at risk of preterm delivery.

Certain embodiments of the invention are directed to methods to reduce transmission of HIV from an HIV/BV or *G. vaginalis*-infected woman to her sexual partner or to a fetus she may be carrying, or to an infant during childbirth by administering a therapeutically effective amount of DNase alone or in combination with one or more antibiotics. Another embodiment is directed to a method for preventing preterm birth in subjects with BV or *G. vaginalis* infections by administering a therapeutically effective amount of DNase and/or antibiotics to a pregnant woman, for example a woman with BV or *G. vaginalis* infections at risk of having a preterm birth. Other embodiments are directed to preventing transmission of an STD from a woman, for example a woman with BV or *G. vaginalis* infection, by administering a therapeutically effective amount of DNase and/or antibiotics.

Other embodiments are directed to methods for preventing or treating postpartum endometritis in subjects with BV or *G. vaginalis* infections by administering a therapeutically effective amount of DNase and/or antibiotics.

Pharmaceutical Compositions

The present invention also includes pharmaceutical compositions and formulations of the DNase and one or more antibiotics that treat BV and *G. vaginalis* infections and other conditions described herein. In an embodiment, the pharmaceutical compositions of the present invention comprise DNase, or DNase and one or more antibiotics in an amount sufficient to prevent or treat the diseases described herein in a subject, formulated for local vaginal administration (such as a suppository) for prophylaxis or therapy for any of the described diseases or conditions. These pharmaceutical compositions may be in the form of a kit. The subject is preferably a human but can be non-human as well. A suitable subject can be an individual who is suspected of having, has been diagnosed as having, or is at risk of developing one of the described diseases.

The therapeutic agent can be formulated into any topical composition known in the art that is suitable for its intended use as described herein, including creams, lotions, ointments, gels, lubricants (described in Porat, U.S. Pat. No. 624,198), liquids, sprays, powders, or absorbent materials.

A composition of the therapeutic agents for topical administration can also include a pharmaceutically acceptable carrier. As used herein the language "pharmaceutically acceptable carrier" includes solvents, dispersion media, coatings, antiviral agents, antibacterial agents, antifungal agents, isotonic and absorption delaying agents, and the like, compatible with pharmaceutical administration. Supplementary active compounds can also be incorporated into the compositions. Other topical formulations are described in Sheele et al., U.S. Pat. No. 7,151,091.

Therapeutic compositions may contain, for example, such normally employed additives as binders, fillers, carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like. These compositions typically contain 1%-95% of active ingredient, preferably 2%-70% active ingredient.

The therapeutic agents can also be mixed with diluents or excipients which are compatible and physiologically tolerable. Suitable diluents and excipients are, for example, water, saline, dextrose, glycerol, or the like, and combinations thereof. In addition, if desired, the compositions may contain minor amounts of auxiliary substances such as wetting or emulsifying agents, stabilizing or pH buffering agents.

In some embodiments, the therapeutic compositions of the present invention are prepared either as liquid solutions or suspensions, as sprays, or in solid forms including but not limited to gels and capsules. The formulations may include such normally employed additives such as binders, fillers, carriers, preservatives, stabilizing agents, emulsifiers, buffers and excipients as, for example, pharmaceutical grades of mannitol, lactose, starch, magnesium stearate, sodium saccharin, cellulose, magnesium carbonate, and the like. These compositions take the form of solutions, suspensions (such as a douche), suppositories, or sustained release formulations, and typically contain 1%-95% of active ingredient, preferably 2%-70%.

Formulations which are suitable for topical administration to the vagina include salves, tinctures, creams, lotions, pessary, transdermal patches, ointments, gels, lubricants, liquid, sprays, powders, absorbent materials, and suppositories. For salves and creams, traditional binders, carriers and excipients may include, for example, polyalkylene glycols or triglycerides. One example of a topical delivery method is described in U.S. Pat. No. 5,834,016. Other liposomal delivery methods may also be employed (See, e.g., U.S. Pat. Nos. 5,851,548 and 5,711,964. The composition can include an inert carrier. The composition can be impregnated in a towlette, sponge or capsule.

The formulations may also contain more than one active compound as necessary for the particular indication being treated, preferably those with complementary activities that do not adversely affect each other. Such molecules are suitably present in combination in amounts that are effective for the purpose intended.

Sustained-release preparations may also be prepared. Suitable examples of sustained release preparations include semipermeable matrices of solid hydrophobic polymers containing the therapeutic agents, which matrices are in the form of shaped articles, e.g., films, or microcapsule. Examples of sustained release matrices include, but are not limited to, polyesters, hydro gels (for example, poly(2-hydroxyethylmethacrylate), or poly(vinylalcohol)), polylactides, copolymers of L-glutamic acid and y ethyl-L-glutamate, non-degradable ethylene-vinyl acetate, degradable lactic acid-glycolic acid copolymers such as the LUPRON DEPOT (injectable micro spheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

The therapeutic agents of the present invention may be administered by any suitable means. DNase is applied locally to the vagina to prevent nonspecific degradation of unintended targets, but antibiotics can be administered systemically as well as locally. For the prevention or treatment of disease, the appropriate dosage will depend on the severity of the disease, whether the drug is administered for protective or therapeutic purposes, previous therapy, the patient's clinical history and response to the drugs and the discretion of the attending physician.

The duration of treatment can extend over several days or longer, depending on the condition, with the treatment continuing until the symptoms of *G. vaginalis* or BV are sufficiently reduced or eliminated. The progress of this therapy is easily monitored by conventional techniques and assays, and may be used to adjust dosage to achieve a therapeutic effect.

III. EXAMPLES

Methods and Materials

Biofilms of multiple *Gardnerella* strains [*G. Vaginalis* is the only species in the genus *Gardnerella*.] were grown, separately, in vitro in 96-well plates in BHI-supplemented media. Bovine pancreas DNase was added in varying concentrations to biofilm cultures at 0 hours (newly forming biofilms) and 24 hours (established biofilms.) The biofilms were washed, the supernatant was removed, and the biofilms were stained with safranin and solubilized in acetic acid. Biofilm absorbance at A462 nm was measured with a spectrophotometer, which method quantifies the amount of safranin stain taken up by the biofilm. DNase-treated and untreated biofilms were also grown in chamber slides and DAPI staining was performed for fluorescence microscopy.

Microscopy

Overnight cultures were prepared as above and rather than inoculated into 96-well plates, were diluted 10-fold and 3 ml volumes inoculated into sterile glass-bottom dishes with either 100 µg/mL of DNase or vehicle control. Dishes were incubated 24 hours and excess media was then removed and the biofilms were washed as above. Biofilms were then stained with propridium iodide and examined with an inverted fluorescent scope (Zeiss) by 2-D imaging as well as 3-D Z-stacking+deconvolution.

Antibiotic Susceptibility Methods

Minimum Inhibitory Concentrations (MICs) for metronidazole and clindamycin for strains 49145 and ARG3 were determined using E-test on Mueller-Hinton agar with 5% sheep's blood by CLSI methodology. Ranges used were based on the MICs of the strains used, with a range from 0.25×-4× the MIC used. Metronidazole MICs=4 for both strain 49145 and strain ARG3. Clindamycin MICs=0.016 and 32 for 49145. Clindamycin MICs=0.125 for strain ARG3. MICs are repeated twice.

Biofilms were grown in the presence of varying concentrations of antibiotic and DNase administered at t=0 hours to test the effect of the agents on biofilm formation. To test the effects on the degradation of established biofilms, the agents were administered at t=24 hours.

All cultures and biofilms were grown in 'biofilm media' (BHI media+0.3% starch, 0.3% glucose, 0.5 mcg/mL amphotericin B) at 37° C. and 5% $CO_2$. Liquid cultures of strains 49145 or ARG3 were grown overnight to a standardized OD600 of 0.6 and diluted 1:10 prior to aliquoting for biofilms. Cultures were aliquoted into 96-well plates as follows:

Testing Inhibition of Newly Forming Biofilms

For DNase Experiments Alone:

180 µL of bacteria and 20 µL of DNase at varying concentrations (1:10 dilutions of 1 mg/mL to final concentrations in the wells as labeled in the figures) or PBS as a control (total volume always 200 µL) were added together at t=0 hours and incubated for 24 hours. They were then washed, stained with safranin and solubilized with ascetic acid, with measurement of absorbance at 462 nm to quantify density of stained material.

For DNase-Antibiotic Experiments:

160 µL of culture, 204 of antibiotic at varying concentrations (1:10 and 2-fold dilutions to final concentrations in wells as labeled in the figures), and 20 µL of DNase at varying concentrations (1:10 dilutions as above) with 20-40 µL of PBS used when necessary for controls (wells without antibiotic, DNase, or both) were added to wells at t=0 hours and incubated for 24 hours as above. Biofilms were quantified as above.

Testing Inhibition of Established Biofilms

For Testing of Dissolution of Established Biofilms:

Experiments were performed similarly to above with the following additional step: All biofilms were grown as full 200 µL liquid cultures in 96-well plates for 24 hours. These resulting biofilms were washed with PBS and then fresh media was added with either DNase alone or DNase in combination with antibiotic as outlined above, again, to a total volume of 200 µL. These cultures/biofilms were again incubated for 24 hours and then stained and solubilized.

For quantification as above, antibiotic concentrations were chosen based on the MIC (⅛-4× MIC).

Statistical Analysis

Statistical comparisons were performed using two-tailed unpaired t-tests or one-way analysis of variance (ANOVA) with Tukey post-test as appropriate (Prism, GraphPad Software).

Example 1

Addition of DNase

The results depicted in FIG. 1 show the dose-response inhibition of *Gardnerella* biofilm formation by bovine pancreatic DNase that was administered (time=0 hours) as assessed by measuring the absorbance of light at 462 nm (A462). A dramatic reduction in the extent of biofilm formation can be seen with DNase applied at 10 µg/ml and 100 µg/ml.

The results depicted in FIG. 2 show the dose-response inhibition of *Gardnerella* strain ARG3 biofilm formation by bovine pancreatic DNase that was administered (time=0 hours) as assessed by measuring the % biofilm density (y axis). Again, a dramatic reduction in the extent of biofilms formation can be seen with DNase applied at 10 µg/ml and 100 µg/ml. Accompanying the reduction in biofilm formation is a parallel dose-dependent breakdown of established *Gardnerella* strain 49145 and ARG3 biofilms by DNase administered at t=24 hours. FIGS. 3 and 4 respectively.

The results depicted in FIG. 17 show the dose-response inhibition of group B *Streptococcus* biofilm formation by DNase that was administered at t=0 hours as assessed by measuring the absorbance of light at 462 nm (A462). A dramatic reduction in the extent of biofilm formation can be seen with DNase applied at 100 µg/ml.

It is important to note that any DNase may be used in the present inventions, including bovine, human DNase, and *Gardnerella* DNase. Routine experimentation will determine the best DNase and therapeutically effective amount to be used depending on the condition and the subject, as described below.

Example 2

Combined Administration of DNase and Antibiotics

Further experiments were conducted to assess whether there is an improved effect on biofilm formation and breakdown by the combined administration of DNase and antibiotics against *Gardnerella*. The y axis plots the % of biofilm absorbance A462 for each condition. Biofilms were grown and measured as above with the addition of varying concentrations of metronidazole and clindamycin and DNase as indicated below. The minimum inhibitory concentration (MIC) for the antibiotics was measured by E-testing the relevant strains. Colony counts were performed on both the supernatant and the biofilm components of the culture, and a one-way ANOVA with Bonferroni post-tests were performed using Prism (Graphpad) where DNase was administered at time=24 hours. Fluorescence microscopy demonstrated a decrease in the biofilm matrix and in overall density in DNase-treated biofilms.

In addition, heat-inactivated DNase did not inhibit the formation of biofilms, consistent with a requirement for enzymatic function for the anti-biofilm effect. FIG. 5.

FIGS. 6 and 8 (C) show the additive and synergistic inhibition respectively of strain 49145 *Gardnerella* biofilm formation by administering metronidazole alone, DNase alone and DNase-metronidazole combined at t-0 hours. The first three bars on the left of FIG. 6 show the effect on biofilm formation of DNase alone by measuring the % biofilm density (y axis). Administering DNase alone at concentrations of 1 µg/mL and 100 µg/mL caused a 30% and 75% reduction in biofilm formation respectively. FIG. 6. In all cases adding DNase together with antibiotic caused an additive improvement in the reduction of *Gardnerella* biofilm formation observed compared to any concentration of antibiotic administered alone. The optimum result for reducing biofilm formation with a DNase/antibiotic combination was achieved with 8 µg/mL metronidazole plus 1 µg/mL DNase where the reduction was about 70%. FIG. 6. The first two bars on the left of FIG. 8 (C) show the effect on biofilm formation of DNase alone as assessed by measuring the absorbance of light at 462 nm (A462). Administering DNase alone at a concentration of 1 µg/mL caused a 30% reduction in biofilm formation. With the addition of 2 µg/mL metronidazole plus 1 µg/mL DNase, the reduction was about 45%. Adding the DNase together with the metronidazole caused a synergistic improvement in the reduction of *Gardnerella* biofilm formation observed compared to the concentration of antibiotic administered alone.

The co-administration of metronidazole and DNase was even more effective in reducing ARG3 biofilm formation where it had a synergic effect when administered at t=0 hours. FIGS. 7 and 8(D) show that as little as 1 µg/ml of DNase administered together with 1 µg/ml metronidazole reduced biofilm formation by about 50% compared to administering antibiotic alone.

The co-administration of clindamycin and DNase was also effective in reducing ARG3 biofilm formation where it had a synergistic effect when administrated at t=0 hours. FIG. 8 (B) shows that 1 µg/ml of DNase administered together with 8 µg/ml clindamycin reduced biofilm formation by about 60% compared to administering antibiotic alone. FIG. 12 shows that 10 µg/ml and 100 µg/ml of DNase administered together with 5.7 µg/ml clindamycin reduced biofilm formation by about 50% and 65% respectively compared to administering antibiotic alone.

The effect of DNase administered together with metronidazole on the breakdown of established *Gardnerella* biofilms was assessed. A synergistic breakdown of established strains 49145 and ARG3 biofilms were seen when a combination of 4 µg/mL metronidazole and 1 µg/mL DNase was administered at t=24 hours. FIGS. 9, 10, and 11(B)-(C). These findings have been replicated using clindamycin. FIG. 11 (A).

Example 3

Liberation of Bacteria into Supernatant

Other in vitro experiments have been conducted showing that treatment with DNase does not reduce the number of bacteria in the biofilm cultures overall. In other words DNase does not kill the bacteria. However, DNase does cause the bacteria embedded in the ATCC *Gardnerella* strain 49145 biofilms to be released into the supernatant. FIGS. 13-15. Thus, while the reductive effect on biofilm formation of *G. vaginalis* strain 49145 is equivalent between treatment with 100 µg/mL of DNase alone and the combination of 1 µg/mL of DNase+16 µg/mL of metronidazole, the overall effect on bacterial killing is very different: DNase does not kill the bacteria and bacteria are killed by the antibiotic in the combination treatment. As more DNase is added to a *Gardnerella* biofilm, increasing numbers of living bacteria are liberated from the biofilm into the media above them. It is these released bacteria that are then able to be killed by the added antibiotic because they are more accessible and therefore more vulnerable to recognition and destruction by antibiotics than are bacteria trapped in a biofilm that would otherwise persist in the biofilm and continue to increase in number. It is possible that treatment of BV and *G. vaginalis* infections with a combination of DNase and antibiotics will permit lower doses of antibiotics to be effective.

Example 4

Murine Models of Vaginal Colonization

The above examples demonstrated the biofilm-inhibiting activity of DNase and its relevance to reproductive tract pathogens in vitro. The same strategy works in the complex environment of the lower genital tract in murine models of vaginal colonization. Models for vaginal colonization of mice with *G. Vaginalis* and group B *Streptococcus* have been developed. Co-inocuation with DNase inhibited the establishment of colonization in ARG37. FIG. 16. These models will important in prophylactic use in at-risk populations including, but not limited to, pregnant women, those individuals infected with sexually transmitted diseases including HIV, and those individuals with recurrent BV.

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than a restrictive sense.

The invention is illustrated herein by the experiments described above, which should not be construed as limiting. The contents of all references, pending patent applications and published patents, cited throughout this application are hereby expressly incorporated by reference. Those skilled in the art will understand that this invention may be embodied in many different forms and should not be construed as limited to the embodiments set forth herein. Rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

REFERENCES

Each of the following references is hereby incorporated by reference as if fully set forth herein, except for terminology that is inconsistent with the terminology used herein.

1. Aroutcheva, A. A., J. A. Simoes, K. Behbakht, and S. Faro. 2001. *Gardnerella vaginalis* isolated from patients with bacterial vaginosis and from patients with healthy vaginal ecosystems. Clin Infect Dis 33:1022-7.
2. Billington, S. J., B. H. Jost, W. A. Cuevas, K. R. Bright, and J. G. Songer. 1997. The *Arcanobacterium* (*Actinomyces*) pyogenes hemolysin, pyolysin, is a novel member of the thiol-activated cytolysin family. J Bacteriol 179:6100-6.
3. Billington, S. J., J. G. Songer, and B. H. Jost. 2002. The variant undecapeptide sequence of the *Arcanobacterium pyogenes* haemolysin, pyolysin, is required for full cytolytic activity. Microbiology 148:3947-54.
4. Bradshaw, C. S., A. N. Morton, J. Hocking, S. M. Garland, M. B. Morris, L. M. Moss, L. B. Horvath, I. Kuzevska, and C. K. Fairley. 2006. High recurrence rates of bacterial vaginosis the course of 12 months after oral metronidazole therapy and factors associated with recurrence. J Infect Dis 193:1478-86.
5. Catlin, B. W. 1992. *Gardnerella vaginalis*: characteristics, clinical considerations, and controversies. Clin Microbiol Rev 5:213-37.
6. Cauci, S., J. F. Culhane, M. Di Santolo, and K. McCollum. 2007. Among pregnant women with bacterial vaginosis, the hydrolytic enzymes sialidase and prolidase are positively associated with interleukin-1beta. Am J Obstet Gynecol.
7. Cauci, S., S. Guaschino, D. De Aloysio, S. Driussi, D. De Santo, P. Penacchioni, and F. Quadrifoglio. 2003. Interrelationships of interleukin-8 with interleukin-1beta and neutrophils in vaginal fluid of healthy and bacterial vaginosis positive women. Mol Hum Reprod 9:53-8.
8. Cauci, S., R. Monte, M. Ropele, C. Missero, T. Not, F. Quadrifoglio, and G. Menestrina. 1993. Pore-forming and haemolytic properties of the *Gardnerella vaginalis* cytolysin. Mol Microbiol 9:1143-55.
9. Criswell, B. S., C. L. Ladwig, H. L. Gardner, and C. D. Dukes. 1969. *Haemophilus vaginalis*: vaginitis by inoculation from culture. Obstet Gynecol 33:195-9.
10. Eschenbach, D. A. 1993. History and review of bacterial vaginosis. Am J Obstet Gynecol 169:441-5.
11. Florez, C., B. Muchada, M. C. Nogales, A. Aller, and E. Martin. 1994. Bacteremia due to *Gardnerella vaginalis*: report of two cases. Clin Infect Dis 18:125.
12. Fredricks, D. N., T. L. Fiedler, and J. M. Marrazzo. 2005. Molecular identification of bacteria associated with bacterial vaginosis. N Engl J Med 353:1899-911.
13. Gardner, H. L., and C. D. Dukes. 1955. *Haemophilus vaginalis* vaginitis: a newly defined specific infection previously classified non-specific vaginitis. Am J Obstet Gynecol 69:962-76.
14. Gardner, H. L., and C. D. Dukes. 1954. New etiologic agent in nonspecific bacterial vaginitis. Science 120:853.
15. Giddings, K. S., J. Zhao, P. J. Sims, and R. K. Tweten. 2004. Human CD59 is a receptor for the cholesterol-dependent cytolysin intermedilysin. Nat Struct Mol Biol 11:1173-8.
16. Greenwood, J. R., and M. J. Pickett. 1979. Salient features of *Haemophilus vaginalis*. J Clin Microbiol 9:200-4.
17. Hadders, M. A., D. X. Beringer, and P. Gros. 2007. Structure of C8alpha-MACPF reveals mechanism of membrane attack in complement immune defense. Science 317:1552-4.
18. Hillier, S. L. 2005. The complexity of microbial diversity in bacterial vaginosis. N Engl J Med 353:1886-7.
19. Huffman, D. L., L. Abrami, R. Sasik, J. Corbeil, F. G. Van der Goot, and R. V. Aroian. 2004. Mitogen-activated protein kinase pathways defend against bacterial pore-forming toxins. Proc Natl Acad Sci USA 101:10995-1000.
20. Hyman, R. W., M. Fukushima, L. Diamond, J. Kumm, L. C. Giudice, and R. W. Davis. 2005. Microbes on the human vaginal epithelium. Proc Natl Acad Sci USA 102:7952-7.
21. Ito, Y., I. Kawamura, C. Kohda, H. Baba, T. Kimoto, I. Watanabe, T. Nomura, and M. Mitsuyama. 2001. Difference in cholesterol-binding and cytolytic activities between listeriolysin O and seeligeriolysin O: a possible role of alanine residue in tryptophan-rich undecapeptide. FEMS Microbiol Lett 203:185-9.
22. Johnson, A. P., C. A. Ison, C. M. Hetherington, M. F. Osborn, G. Southerton, W. T. London, C. S. Easmon, and D. Taylor-Robinson. 1984. A study of the susceptibility of three species of primate to vaginal colonization with *Gardnerella vaginalis*. Br J Exp Pathol 65:389-96.
23. Johnson, A. P., C. A. Ison, C. M. Hetherington, M. F. Osborn, G. Southerton, W. T. London, C. S. Easmon, and D. Taylor-Robinson. 1984. Vaginal colonization of pig-tailed macaques by *Gardnerella vaginalis*. Scand J Urol Nephrol Suppl 86:207-10.
24. Korchev, Y. E., C. L. Bashford, C. Pederzolli, C. A. Pasternak, P. J. Morgan, P. W Andrew, and T. J. Mitchell. 1998. A conserved tryptophan in pneumolysin is a determinant of the characteristics of channels formed by pneumolysin in cells and planar lipid bilayers. Biochem J 329 (Pt 3):571-7.
25. Leopold, S. 1953. Heretofore undescribed organism isolated from the genitourinary system. US Armed Forces Med J 4:263-6.
26. Mardh, P. A., E. Holst, and B. R. Moller. 1984. The grivet monkey as a model for study of vaginitis. Challenge with 26. anaerobic curved rods and *Gardnerella vaginalis*. Scand J Urol Nephrol Suppl 86:201-5.
27. McDonald, H. M., P. Brocklehurst, and A. Gordon. 2007. Antibiotics for treating bacterial vaginosis in pregnancy. Cochrane Database Syst Rev:CD000262.
28. Nagamune, H., K. Ohkura, A. Sukeno, G. Cowan, T. J. Mitchell, W. Ito, O. Ohnishi, K. Hattori, M. Yamato, K. Hirota, Y. Miyake, T. Maeda, and H. Kourai. 2004. The human-specific action of intermedilysin, a homolog of streptolysin O, is dictated by domain 4 of the protein. Microbiol Immunol 48:677-92.
29. Nagamune, H., C. Ohnishi, A. Katsuura, K. Fushitani, R. A. Whiley, A. Tsuji, and Y. Matsuda. 1996. Intermedilysin, a novel cytotoxin specific for human cells secreted by *Streptococcus intermedius* UNS46 isolated from a human liver abscess. Infect Immun 64:3093-100.
30. Piot, P., E. van Dyck, M. Goodfellow, and S. Falkow. 1980. A taxonomic study of *Gardnerella vaginalis* (*Haemophilus vaginalis*) Gardner and Dukes 1955. J Gen Microbiol 119:373-96.
31. Polekhina, G., K. S. Giddings, R. K. Tweten, and M. W. Parker. 2005. Insights into the action of the superfamily of cholesterol-dependent cytolysins from studies of intermedilysin. Proc Natl Acad Sci USA 102:600-5.
32. Ratner, A. J., K. R. Hippe, J. L. Aguilar, M. H. Bender, A. L. Nelson, and J. N. Weiser. 2006. Epithelial cells are sensitive detectors of bacterial pore-forming toxins. J Biol Chem 281:12994-8.
33. Reimer, L. G., and L. B. Reller. 1984. *Gardnerella vaginalis* bacteremia: a review of thirty cases. Obstet Gynecol 64:170-2.
34. Rosado, C. J., A. M. Buckle, R. H. Law, R. E. Butcher, W. T. Kan, C. H. Bird, K. Ung, K. A. Browne, K. Baran, T. A. Bashtannyk-Puhalovich, N. G. Faux, W. Wong, C. J. Porter, R. N. Pike, A. M. Ellisdon, M. C. Pearce, S. P. Bottomley, J. Emsley, A. I. Smith, J. Rossjohn, E. L. Hartland, I. Voskoboinik, J. A. Trapani, P. I. Bird, M. A. Dunstone, and J. C. Whisstock. 2007. A common fold mediates vertebrate defense and bacterial attack. Science 317:1548-51.
35. Rottini, G., A. Dobrina, O. Forgiarini, E. Nardon, G. A. Amirante, and P. Patriarca. 1990. Identification and partial characterization of a cytolytic toxin produced by *Gardnerella vaginalis*. Infect Immun 58:3751-8.
36. Sadhu, K., P. A. Domingue, A. W. Chow, J. Nelligan, N. Cheng, and J. W. Costerton. 1989. *Gardnerella vaginalis* has a gram-positive cell-wall ultrastructure and lacks classical cell-wall lipopolysaccharidE. J Med Microbiol 29:229-35.
37. Saunders, F. K., T. J. Mitchell, J. A. Walker, P. W. Andrew, and G. J. Boulnois. 1989. Pneumolysin, the thiol-activated toxin of *Streptococcus pneumoniae*, does not require a thiol group for in vitro activity. Infect Immun 57:2547-52.
38. Tweten, R. K. 2005. Cholesterol-dependent cytolysins, a family of versatile pore-forming toxins. Infect Immun 73:6199-209.
39. Witkin, S. S., I. M. Linhares, P. Giraldo, and W. J. Ledger. 2007. An altered immunity hypothesis for the development of symptomatic bacterial vaginosis. Clin Infect Dis 44:554-7.
40. Eschenbach D A, Gravett M G, Chen K C, Hoyme U B, Holmes K K. Bacterial vaginosis during pregnancy. An association with prematurity and postpartum complications. Scand J Urol Nephrol Suppl. 1984; 86:213-222.
41. Hillier S L, Nugent R P, Eschenbach D A, et al. Association between bacterial vaginosis and preterm delivery of a low-birth-weight infant. The Vaginal Infections and Prematurity Study Group. N Engl J Med. Dec. 28, 1995; 333(26):1737-1742.
42. Watts D H, Eschenbach D A, Kenny G E. Early postpartum endometritis: the role of bacteria, genital mycoplasmas, and *Chlamydia trachomatis*. Obstet Gynecol. January 1989; 73(1):52-60.
43. Cohen C R, Duerr A, Pruithithada N, et al. Bacterial vaginosis and HIV seroprevalence among female commercial sex workers in Chiang Mai, Thailand. Aids. September 1995; 9(9):1093-1097.
44. Taha T E, Hoover D R, Dallabetta G A, et al. Bacterial vaginosis and disturbances of vaginal flora: association with increased acquisition of HIV. Aids. Sep. 10, 1998; 12(13):1699-1706.
45. Martin H L, Richardson B A, Nyange P M, et al. Vaginal lactobacilli, microbial flora, and risk of human immunodeficiency virus type 1 and sexually transmitted disease acquisition. J Infect Dis. December 1999; 180(6):1863-1868.
46. Koumans E H, Kendrick J S. Preventing adverse sequelae of bacterial vaginosis: a public health program and research agenda. Sex Transm Dis. May 2001; 28(5):292-297.
47. Gardner H L, Dukes C D. *Haemophilus vaginalis* vaginitis: a newly defined specific infection previously classified non-specific vaginitis. Am J Obstet Gynecol. May 1955; 69(5):962-976.
48. Josey W E, Schwebke J R. The polymicrobial hypothesis of bacterial vaginosis causation: a reassessment. Int J STD AIDS. March 2008; 19(3):152-154.
49. Schwebke J R, Rivers C, Lee J. Prevalence of *Gardnerella vaginalis* in Male Sexual Partners of Women With and Without Bacterial Vaginosis. Sex Transm Dis. Sep. 10, 2008.
50. Gelber S E, Aguilar J L, Lewis K L, Ratner A J. Functional and phylogenetic characterization of Vaginolysin, the human-specific cytolysin from *Gardnerella vaginalis*. J Bacteriol. June 2008; 190(11):3896-3903.
51. Hogan V K, Culhane J F, Hitti J, Rauh V A, McCollum K F, Agnew K J. Relative performance of three methods for diagnosing bacterial vaginosis during pregnancy. Matern Child Health J. November 2007; 11(6):532-539.
52. Amsel R, Totten P A, Spiegel C A, Chen K C, Eschenbach D, Holmes K K. Nonspecific vaginitis. Diagnostic criteria and microbial and epidemiologic associations. Am J Med. January 1983; 74(1):14-22.
53. Keane F E, Maw R, Pritchard C, Ison C A. Methods employed by genitourinary medicine clinics in the United Kingdom to diagnose bacterial vaginosis. Sex Transm Infect. April 2005; 81(2):155-157.
54. Nugent R P, Krohn M A, Hillier S L. Reliability of diagnosing bacterial vaginosis is improved by a standardized method of gram stain interpretation. J Clin Microbiol. February 1991; 29(2):297-301.
55. Tam M T, Yungbluth M, Myles T. Gram stain method shows better sensitivity than clinical criteria for detection of bacterial vaginosis in surveillance of pregnant, low-income women in a clinical settinG. Infect Dis Obstet Gynecol. 1998; 6(5):204-208.
56. Hedges S R, Barrientes F, Desmond R A, Schwebke J R. Local and systemic cytokine levels in relation to changes in vaginal flora. J Infect Dis. Feb. 15, 2006; 193(4):556-562.
57. Donder G G, Vereecken A, Bosmans E, Dekeersmaecker A, Salembier G, Spitz B. Definition of a type of abnormal vaginal flora that is distinct from bacterial vaginosis: aerobic vaginitis. BjoG. January 2002; 109(1):34-43.

58. Myziuk L, Romanowski B, Johnson S C. Blue test for diagnosis of bacterial vaginosis. J Clin Microbiol. May 2003; 41(5):1925-1928.
59. Calderon E, Rivera R, Gordillo S, Conde-Glez C. Evaluation of a fast test to identify the presence of proline aminopeptidase in women with bacterial vaginosis. Infect Dis Obstet Gynecol. 1997; 5(3):226-231.
60. West B, Morison L, Schim van der Loeff M, et al. Evaluation of a new rapid diagnostic kit (FemExam) for bacterial vaginosis in patients with vaginal discharge syndrome in The Gambia. Sex Transm Dis. June 2003; 30(6):483-489.
61. Fredricks D N, Fiedler T L, Thomas K K, Mitchell C M, Marrazzo J M. Changes in Vaginal Bacterial Concentrations with Intravaginal Metronidazole Therapy for Bacterial Vaginosis as Assessed by Quantitative PCR. J Clin Microbiol. Jan. 14, 2009.
62. Menard J P, Fenollar F, Henry M, Bretelle F, Raoult D. Molecular quantification of Gardnerella vaginalis and Atopobium vaginae loads to predict bacterial vaginosis. Clin Infect Dis. Jul. 1, 2008; 47(1):33-43.
63. Briselden A M, Hillier S L. Evaluation of affirm VP Microbial Identification Test for Gardnerella vaginalis and Trichomonas vaginalis. J Clin Microbiol. January 1994; 32(1):148-152.
64. Nelson D B, Hanlon A, Hassan S, et al. Preterm labor and bacterial vaginosis-associated bacteria among urban women. J Perinat Med. Nov. 10, 2008.
65. Klein L L, Gibbs R S. Use of microbial cultures and antibiotics in the prevention of infection-associated preterm birth. Am J Obstet Gynecol. June 2004; 190(6):1493-1502.
66. McDonald H M, Brocklehurst P, Gordon A. Antibiotics for treating bacterial vaginosis in pregnancy. Cochrane Database Syst Rev. 2007(1):CD000262.
67. Eschenbach D A, Gravett M G, Chen K C, Hoyme U B, Holmes K K. Bacterial vaginosis during pregnancy. An association with prematurity and postpartum complications. Scand J Urol Nephrol Suppl. 1984; 86:213-222.
68. Hillier S L, Nugent R P, Eschenbach D A, et al. Association between bacterial vaginosis and preterm delivery of a low-birth-weight infant. The Vaginal Infections and Prematurity Study Group. N Engl J Med. Dec. 28, 1995; 333 (26):1737-1742.
69. Watts D H, Eschenbach D A, Kenny G E. Early postpartum endometritis: the role of bacteria, genital mycoplasmas, and Chlamydia trachomatis. Obstet Gynecol. January 1989; 73(1):52-60.
70. Cohen C R, Duerr A, Pruithithada N, et al. Bacterial vaginosis and HIV seroprevalence among female commercial sex workers in Chiang Mai, Thailand. Aids. September 1995; 9(9):1093-1097.
71. Taha T E, Hoover D R, Dallabetta G A, et al. Bacterial vaginosis and disturbances of vaginal flora: association with increased acquisition of HIV. Aids. Sep. 10, 1998; 12(13):1699-1706.
72. Martin H L, Richardson B A, Nyange P M, et al. Vaginal lactobacilli, microbial flora, and risk of human immunodeficiency virus type 1 and sexually transmitted disease acquisition. J Infect Dis. December 1999; 180(6):1863-1868.
73. O'Toole G., Kaplan H B, Kolter R (2000) Biofilm formation as microbial development. Annju Rev Microbiol 54: 49-79.
74. Patterson, et al., Effect of biofilm phenotype on resistance of G. vaginalis to hydrogen peroxide and lactic acid, Am. J. Obstet. Gynecol 2007; 197:170.e1-170.e7.
75. Schwebke, J R, Desmond, R A. A randomized trial of the duration of therapy with metronidazole plus or minus azithromycin for treatment of symptomatic bacterial vaginosis. Clin Infect Dis 2007; 44:213.
76. Paavonen, J, Mangioni, C, Martin, M A, Wajszczuk, C P. Sexually Transmitted Diseases Treatment Guidelines, 2006. MMWR Recomm Rep 006. (RR-11); 55:1-95.
77. Anonymous. Tinidazole (Tindamax)—a new option for treatment of bacterial vaginosis. Med Lett Drugs Ther 2007; 49:73.
78. Gelber, S E, Aguilar, J L, Lewis, K L T, Ratner, A J. Functional and Phylogenetic Characterization of Vaginolysin, the Human-Specific Cytolysin from Gardnerella vaginalis. Copyright© American Society for Microbiology, J Bacteriol., June 2008, p. 3896-3903, doi: 10.1128/JB.01965-07.
79. Chohan, L, Hollier, L M, Bishop K, Kilpatrick C C. Patterns of Antibiotic Resistance Among Group B Streptococcus Isolates: 2001-2004. Infec Dis Obstet Gynecol. 2006; 2006: 57492. Published Online 2006 Mar. 19.
80. DeBacker, E, Verhelst, R, Verstraelen, H, Claeys, G, Verschraegen, G, Temmerman, M, Vaneechoutte, M. Antibiotic susceptibility of Atopobium vaginae: BMC Infectious Diseases 2006, 6: 51.
81. Nyirjesy, P, McIntosh M J, Steinmetz J I, Schumacher R J, Joffnon J L. The effects of intravaginal clindamycin and metronidazole therapy on vaginal mobiluncus morphotypes in patients with bacterial vaginosis. Sex Transm Dis. 2007 April; 34 (4) 197-202.

What is claimed is:

1. A method for treating bacterial vaginosis or Gardnerella vaginalis infections in a subject comprising locally administering to a vagina in the subject a therapeutically effective amount of DNase and either locally or systemically administering a therapeutically effective amount of an antibiotic selected from the group consisting of metronidazole, clindamycin, and tinidazole in an amount that achieves an in vivo concentration of from 0.25-times to 4-times the minimum inhibitory concentration of each respective antibiotic.

2. The method of claim 1, wherein the DNase and the antibiotic are administered at the same time.

3. The method of claim 1, wherein the DNase is administered topically to the vagina.

4. The method of claim 1, wherein the DNase and antibiotic are repeatedly administered until the symptoms of the bacterial vaginosis or G. vaginalis infection are reduced or gone.

5. The method of claim 1, wherein the therapeutically or prophylactically effective amount of DNase is from about 1 µg/ml to 100 µg/ml.

6. The method of claim 1, wherein the therapeutically or prophylactically effective amount of DNase is from 1 mg to about 25 mg.

7. The method of claim 6, wherein the therapeutically or prophylactically effective amount of DNase is about 2.5 mg.

* * * * *